United States Patent [19]

Perkins et al.

[11] Patent Number: 5,222,966
[45] Date of Patent: Jun. 29, 1993

[54] BALLOON CONNECTION AND INFLATION LUMEN FOR ATHERECTOMY CATHETER

[75] Inventors: Roger W. Perkins, Fremont; Gerri L. Chatelain, Pleasanton, both of Calif.

[73] Assignee: Devices for Vascular Intervention, Inc., Redwood City, Calif.

[21] Appl. No.: 845,124

[22] Filed: Mar. 3, 1992

Related U.S. Application Data

[63] Continuation-in-part of Ser. No. 486,675, Feb. 28, 1990, Pat. No. 5,092,873.

[51] Int. Cl.$^5$ .............................. A61B 17/20
[52] U.S. Cl. .................... 606/159; 606/170; 606/194; 604/96; 604/103
[58] Field of Search .............. 606/7, 159, 170, 180, 606/191, 192, 194; 604/22, 96, 101, 103

[56] References Cited

U.S. PATENT DOCUMENTS

| | | | |
|---|---|---|---|
| 4,669,469 | 6/1987 | Gifford, III et al. | 606/170 |
| 5,002,532 | 3/1991 | Gaiser et al. | 606/194 |
| 5,026,366 | 6/1991 | Leckrone | 606/7 |

FOREIGN PATENT DOCUMENTS

0163502 12/1985 European Pat. Off. ........... 606/159

Primary Examiner—John D. Yasko
Assistant Examiner—Anthony Gutowski
Attorney, Agent, or Firm—Townsend and Townsend Khourie and Crew

[57] ABSTRACT

A vascular catheter includes a flexible catheter body having proximal and distal ends and an elongate housing secured to the distal end of the catheter body. An interactional device is disposed on one side of the housing, and at least two spaced-apart inflatable chambers are located on the other side of the housing generally at its proximal and distal ends, respectively. The inflatable chambers may be expanded simultaneously or separately, and the spaced-apart positioning of the chambers provides for stable positioning of the housing during atherectomy procedures, imaging procedures, and the like. The balloon is conveniently connected to the housing by an integral flange structure which is secured through an inflation aperture on the housing side. The balloon may be inflated through an annular inflation which is defined by a separate isolation tube disposed in the central lumen of the catheter body.

15 Claims, 5 Drawing Sheets

BALLOON CONNECTION AND INFLATION LUMEN FOR ATHERECTOMY CATHETER

This application is a continuation-in-part of application Ser. No 07/486,675, filed on Feb. 28, 1990, (now U.S. Pat. No. 5,092,873) the disclosure of which is incorporated herein by reference.

BACKGROUND OF THE INVENTION

1. Field of the Invention

The present invention relates generally to the construction of catheters capable of being introduced into a patient's vascular system. In particular, the present invention relates to atherectomy devices which use an inflatable balloon for effecting contact between an interventional or diagnostic implement and the blood vessel wall.

Atherosclerosis is a condition characterized by fatty deposits (atheromas) in the intimal lining of a patient's blood vessels. Atherosclerosis can have many manifestations, including angina, hypertension, myocardial infarction, strokes, and the like. Initially, the atheromas deposited on the blood vessel walls remain relatively soft and tractable. Over time, however, the soft atheromic material becomes a calcified and hardened plaque. Regions of the blood vessel which are blocked by atheroma, plaque, or other material are generally referred to as stenoses, and the blocking material as stenotic material.

Atherectomy is a procedure which has been developed for removing stenotic material from the vascular system, usually before substantial calcification has occurred. Atherectomy procedures can utilize a variety of special catheters having severing instruments located at a distal end thereof and, often, an inflatable balloon for positioning the severing instrument. Usually, the catheter is located within the vascular system so that the severing instrument lies adjacent the stenotic region, and the balloon is inflated to bring the severing instrument into close proximity to the stenotic material. The severing instrument is then actuated to excise the released portion of the stenotic material, and the severed material captured to prevent the release of emboli.

The severing instrument on the atherectomy catheter can take a variety of forms, including fixed blades (requiring movement of the entire catheter to effect cutting) and movable blades which can be actuated within a stationary housing at the distal end of the catheter. Of particular interest to the present invention are atherectomy catheters of the type described in European Patent Application 163 502, owned by the assignee of the present invention. Such atherectomy catheters include a cutter housing attached to the distal end of a torqueable catheter body. A circular cutting blade is disposed within the housing and secured to the distal end of a rotatable drive shaft. An elongate aperture formed on one side of the housing allows the intrusion of stenotic material which may then be severed by rotating and axially translating the cutting blade. An inflatable balloon is disposed on the side of the housing opposite to the aperture so that the housing can be urged against the stenotic material on a blood vessel wall.

Although such atherectomy catheters have enjoyed substantial success and acceptance in the medical community, expansion of the positioning balloon required to laterally shift the cutter housing can have undesired effects on the adjacent blood vessel wall. For example, if the blood vessel wall in contact with the balloon is generally healthy, expansion of the balloon can cause damage. If, as is more likely, there are deposits of stenotic material on the blood vessel wall in contact with the positioning balloon, expansion of the balloon can compress the stenotic material in a manner similar to that of an angioplasty balloon. While such compression is not necessarily harmful, it renders subsequent excision of the stenotic material using the atherectomy catheter much more difficult.

A more serious shortcoming of previous atherectomy positioning balloons has been an inability to stably position the housing during the atherectomy procedure. For example, in tight stenotic regions, expansion of the positioning balloons can cause the cutter housing to be longitudinally displaced from its original position, rendering the desired cut problematic. Moreover, the stenotic material itself may be dislodged from its original position, which can interfere with positioning of the cutter housing and, in a worse instance, cause the release of stenotic material into the blood flow.

An additional concern in the design and construction of atherectomy catheters is the connection of the balloon to the housing and associated inflation lumen. It is desirable that balloon connection be made as simply as possible so that the balloon profile is not increased by the need to incorporate additional adapters, connectors, seals, and the like. It is further desirable that the connection be made very secure and substantially leak proof so that the connection between the balloon and associated inflation lumen will not fail when the balloon is pressurized during use. Finally, it is desirable that the balloon be conformable to a desired balloon geometry even after the balloon has been connected to the atherectomy housing.

For these reasons, it would be desirable to provide improved positioning balloons for atherectomy devices and other catheters. It would be particularly desirable to provide positioning balloons which would allow for stable positioning of a cutter housing or other interventional device within a blood vessel within a wide variety of conditions. Moreover, it would be desirable if such position balloons were inherently less likely to damage or dilitate a blood vessel during performance of an interventional procedure. It would be further desirable to provide improved fabrication techniques which permit the formation and connection of inflation balloons on atherectomy catheters, where the inflation balloons are firmly secured to the housing. It would be even further desirable to provide an atherectomy catheter having an annular inflation lumen which is isolated from the interior of the housing and which does not require a sliding seal to be formed on the drive shaft of the cutting blade.

2. Description of the Background Art and Related Applications

European Patent Application 163 502 is discussed above and corresponds to copending U.S. patent application Ser. No. 07/298,846, the disclosure of which is incorporated herein by reference. Similar atherectomy catheter designs which employ inflatable balloons for positioning a distal housing are described in U.S. Pat. Nos. 4,669,469 (now Re. 33,569); 4,771,774; and 4,781,186, and copending application Ser. Nos. 07/243,397; 07/045,916; and 07/117,072, the disclosures of which are incorporated herein by reference. Reissue patent Re. 33,569 describes an atherectomy catheter having a single inflation lumen extending through the catheter body. The single inflation lumen is isolated from the interior of a cutter housing by an O-ring seal. The inflation balloon is connected to the central inflation lumen in the catheter body by a reinforced extremity formed at one end of the balloon. Angioplasty and other vascular catheters employing spaced-apart balloons at their distal ends are described in U.S. Pat. Nos. 4,573,966; 4,610,662; 4,636,195; and 4,794,928.

SUMMARY OF THE INVENTION

According to the present invention, a catheter comprises a flexible catheter body having a proximal end and a distal end. An elongate housing having a proximal end and a distal end is secured at its proximal end to the distal end of the catheter body, and at least two spaced-apart inflatable chambers are located on one side of the housing at the proximal and distal ends, respectively. A device for interacting with the environment surrounding the catheter housing, typically an atherectomy blade or an imaging device, is provided on a side of the housing opposite to that of the inflatable chambers. A means is provided for inflating the chambers, either separately or simultaneously, and the catheter housing may thus be urged in the direction of the interactional device. The spaced-apart configuration of the inflatable chambers has a number of advantages. Separation of the inflatable chambers provides greater positional stability for the catheter housing within a blood vessel. In particular, the separate inflatable chambers reduces the likelihood that the housing will be "squeezed" from a region of stenosis as the chambers are inflated. A particular advantage of the spaced-apart inflatable chamber configuration is that the likelihood of dilatation and damage to the blood vessel is greatly reduced.

In a first specific embodiment, the two inflatable chambers are interconnected so that inflation by a common inflation lumen results in the substantially simultaneous expansion of both chambers. In a second specific embodiment, inflatable chambers are isolated and inflated by separate inflation lumens. Such a design allows the chambers to be separately expanded, enhancing the ability to position and level the catheter housing within the blood vessel. In a third particular embodiment, the two inflatable chambers are defined by a single inflatable bladder which is divided by an elastic constrictive member. Such a design allows for separate expansion of the chambers initially and for subsequent expansion of the entire bladder by raising the inflation pressure above a predetermined threshold level.

In yet another aspect of the device of the present invention, an inflatable balloon, having either a single chamber or multiple chambers, is secured to a housing at the distal end of the catheter body, typically to the outside of a cutter housing on an atherectomy catheter. The inflatable balloon includes an integral flange structure at its proximal end, where the flange structure is secured through an aperture in the housing so that the balloon can be inflated through a central lumen in the catheter body.

In still another aspect of the present invention, the catheter comprises a flexible catheter body having an elongate housing at its distal end. An isolation tube is disposed inside a central lumen of the catheter body and is secured at its distal end to the interior of the housing. An inflatable balloon is secured to the exterior of the housing and connected to an annular inflation lumen defined between the isolation tube and the interior of the catheter body to permit inflation thereof. A central lumen of the isolation tube is particularly suitable for receiving a drive shaft for connection to an atherectomy blade within the elongate housing. In this way, the drive shaft is available for movement, typically rotation and axial translation, without the need to provide a sliding seal as in certain prior art devices.

According to the method of the present invention, a catheter housing having an aperture on one side is positioned proximate a stenosed region within a patient's vascular system. A pair of axially spaced-apart inflatable chambers located on the side of the housing opposite to that of the aperture is inflated in order to urge stenotic material into the aperture. A cutting blade is then translated across the aperture in order to sever the stenotic material. The inflatable chambers may be inflated to the same or different pressures, depending on the nature of the stenosed region. Optionally, a third segment or chamber located between the proximal and distal inflatable chambers may be inflated on appropriate to improve the positioning of the catheter housing within the blood vessel.

The present invention further provides a method for joining an inflatable balloon to a cylindrical housing having an axial lumen. The method comprises inserting an end of a thermoplastic tube through an aperture in the housing. A rod is then positioned through a lumen of the thermoplastic tube so that an end of the rod is disposed in the interior of the housing. A heated mandrel is then axially inserted into one end of the housing and contacted against the thermoplastic tube to form a saddle-flange which conforms to the interior surface of the housing. The rod acts as a space maintainer to keep the passage through the resulting flange open and available for subsequent balloon inflation. After the saddle joint is formed, the balloon can be formed into a desired geometry, typically by introducing heated air into its interior and molding. Usually, the flange will be glued to the interior surface of the housing, and the proximal end of the balloon will be connected to the housing by any one of a variety of techniques.

DESCRIPTION OF THE SPECIFIC EMBODIMENTS

The vascular catheters of the present invention will include a flexible catheter body which may be similar in construction to a wide variety of vascular catheters of the type which are well known in the art. The flexible catheter body will usually comprise a very flexible tube having proximal and distal ends and on or more lumens extending between said ends. The tube may be formed by extrusion of an organic polymer, typically a thermoplastic, such as nylon, polyurethane, polyethyleneterephthalate (PET), polyvinylchloride (PVC), polyethylene, or the like. The tubes so formed may be reinforced or unreinforced, with reinforcement being provided by metal wires, metal braided cables, or the like. The catheter body will typically have a length in the range from about 60 to 150 cm and a diameter in the range from about 3 to 11 F (F; 0.33 mm). For use in coronary applications, the catheter body will typically have a length from about 120 to 150 cm and a diameter from about 3 to 8 F, while for peripheral applications the catheter body will have a length from about 60 to 110 cm and a diameter from about 3 to 11 F.

An elongate housing having proximal and distal ends will be secured to or formed at the distal end of the catheter body. The elongate housing will usually have a length in the range from about 5 to 40 mm, more usually being in the range from about 15 to 25 mm. The housing may be open, i.e., include one or more apertures, gaps, or the like, which allow for unrestricted passage of materials or energy between the interior of the housing and the external environment surrounding the housing, or may be closed. The housing may be formed separately or integrally with the structure of the catheter body but, in either case, will usually provide a more rigid structure than the catheter body itself. Frequently, the housing will be very rigid, although a certain degree of flexibility may be desirable in certain applications. The construction of flexible elongate housings is described in U.S. Pat. No. 4,781,186, the disclosure of which has previously been incorporated herein by reference. The housing may be formed from metal, such as stainless steel, from a rigid plastic, or may be formed by a reinforcement of the catheter body itself within the region intended as the housing. When intended for atherectomy, the housing will usually have a cylindrical cross section with an elongate aperture formed on one side thereof. A cutting blade will be disposed within the housing for translation past the aperture in order to effect severing of atheroma, as generally described in copending U.S. application Ser. No. 07/298,846, the disclosure of which has previously been incorporated herein by reference.

A wide variety of internal components may be located within the housing in order to provide for various interactional capabilities, particularly interventional and imaging capabilities, such as atherectomy, laser ablation, perfusion, therapeutic ultrasound, endoscopic imaging, ultrasonic imaging, and the like. The present invention will find its greatest use, however, with side-cutting atherectomy devices of the type described in copending application Ser. No. 07/298,846, the disclosure of which has previously been incorporated herein by reference. At least some portion of the interactional mechanism will usually be disposed on one side of the housing so that the housing structure as a whole is non-symmetric. Such non-symmetry will usually require that the catheter be capable of rotational alignment within a blood vessel so that the external component(s) on the housing will lie adjacent at a preselected region, usually a preselected region of stenosis, on the blood vessel wall.

At least the inflatable chambers are disposed on a side of the elongate housing opposite to that on which the interventional component(s) are located. A first of the inflatable chambers will generally be located distally or forwardly of the interventional component(s), while a second of the inflatable chambers will be located proximally or rearwardly of such component(s). More usually, the first inflatable chamber will be located generally at the distal end of the elongate housing, while the second inflatable chamber is located at the proximal end of the housing. Inflation of the chambers will urge the elongate housing in the direction of the interactional components (when the housing is located within a blood vessel), and such spaced-apart configuration affords stable positioning of the housing during an interactional procedure, e.g., atherectomy. Additionally, the spaced-apart inflatable chambers decrease the chance of unintentional dilatation of the blood vessel.

The inflatable chambers may be isolated to allow for separate inflation or may be interconnected to allow for simultaneous inflation. The chambers may have the same or different geometries, and chambers having the same geometry may have the same or different dimensions. When isolated, inflatable chambers will usually require separate inflation lumens within the catheter body, although it will be possible to provide a single inflation lumen which is branched at some point so that it can connect to the two isolated inflatable chambers. Conversely, when the two chambers are interconnected, it will usually be necessary only to provide a single inflation lumen as the inflation medium will enter both chambers. It may be desirable, however, to provide two (or more) inflation lumens for redundancy or other purposes.

Usually, the inflatable chambers will be formed from a thermoplastic or thermosetting plastic which may be formed into a desired geometry by well-known extrusion and thermal shaping techniques. In most cases, a single bladder will be formed which is divided into the two separate chambers, but it will also be possible to form the chambers entirely separately from each other. In the case of a single bladder or balloon, the chambers may be formed by controlling the inflation profile so that two relatively large volumes are formed at either end with a narrower constricted region therebetween. Alternatively, the chamber may be formed with a substantially uniform cross section with a separate constrictive member wrapped around the middle to separate a first chamber from a second chamber. Optionally, the constrictive member may be elastic so that the middle portion of the bladder may be inflated when the inflation pressure exceeds a predetermined threshold level.

Depending on the dimensions of the housing, each inflation chamber will usually have a length in the range from about 2 to 15 mm, more usually being in the range from about 3 to 10 mm, and will be spaced apart by a distance in the range from about 4 to 30 mm, more usually being in the range from about 6 to 20 mm. The cross-sectional areas of each chamber will generally be from about 0.1 to 10 times the cross-sectional area of the housing, more usually being from 0.5 to 2.0 times the cross-sectional area. For cylindrical inflatable chambers, the diameter will usually be in the range from about 1 to 5 mm, more usually being in the range from about 1.5 to 3 mm.

Referring now to FIGS. 1, 2, 3A, and 3B, an atherectomy catheter 10 includes a proximal end 12 and a distal end 14. A manifold connector 16 at the proximal end 12 includes a conventional rotatable fitting 18 joining the manifold 16 to a flexible catheter body 22. An inflation port 24 and a flush port 26 are provided and connected to the catheter body 22, as described in greater detail hereinafter. A driver connection 28 is attached to a cutter torque cable 30 and is able to rotate and axially translate the cable, typically using a motor drive unit (not illustrated) such as that described in U.S. Pat. No. 4,771,774, the disclosure of which has previously been incorporated herein by reference. The design and construction of the manifold connector 16 is conventional and need not be described further. An elongate housing 32 is secured to the distal end of catheter body 22 and includes interactional means, as described in greater detail hereinbelow.

General considerations relating to the design and construction of atherectomy catheters are described in copending applications Ser. No. 07/298,846 and 07/405,906, the disclosures of which are incorporated herein by reference.

Figure 1:
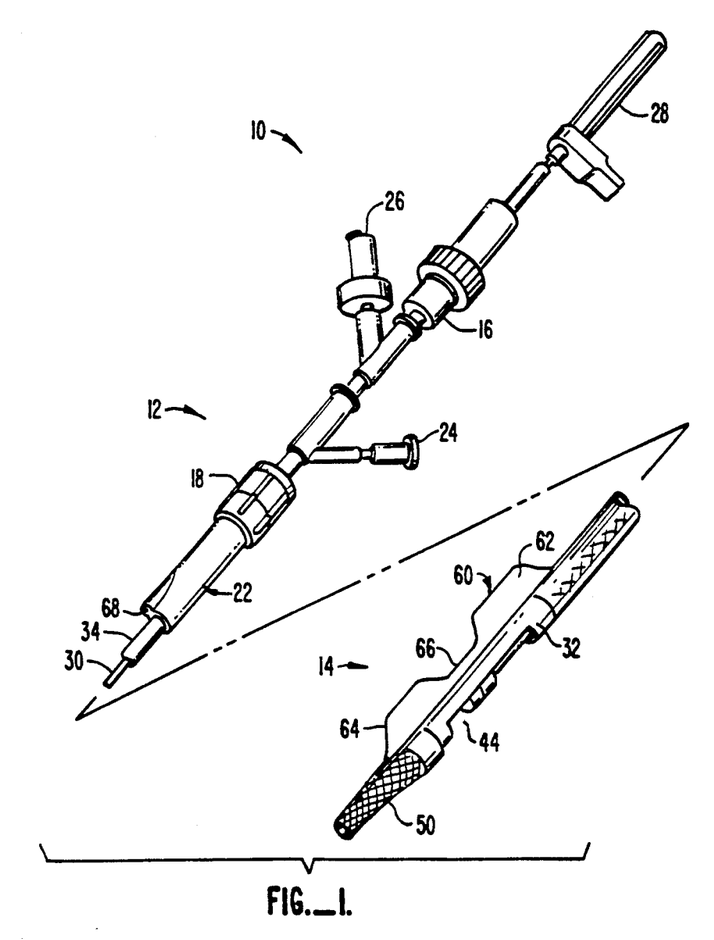
FIG. 1 is a perspective view of a catheter constructed in accordance with the principles of the present invention, shown with portions broken away.

The catheter body 22 is that portion of the atherectomy catheter 10 which extends from the manifold connector 16 to the elongate housing 32 secured at its distal end. Catheter body 22 includes a flexible torque member 34 which is fixedly attached to the manifold connector 16 so that rotation of the rotational fitting 18 will result in rotation of the catheter body 22 along its entire length, further resulting in rotation of the elongate housing 32.

The flexible torque member 34 will normally be a braided metal cable, typically a stainless steel braided cable, as described in copending application Ser. No. 07/298,846, the disclosure of which has previously been incorporated herein by reference. It is important that the flexible torque member 34 be highly flexible, yet remain capable of transmitting torque along its entire length with a minimal loss of transmission efficiency. The diameter of the flexible torque member 34 will vary depending on the intended application of the catheter 10, generally being in the range from about 1 mm to 4 mm, usually being in the range from about 2 mm to 4 mm for peripheral arteries and in the range from about 1 mm to 2 mm for coronary arteries.

Figure 2:
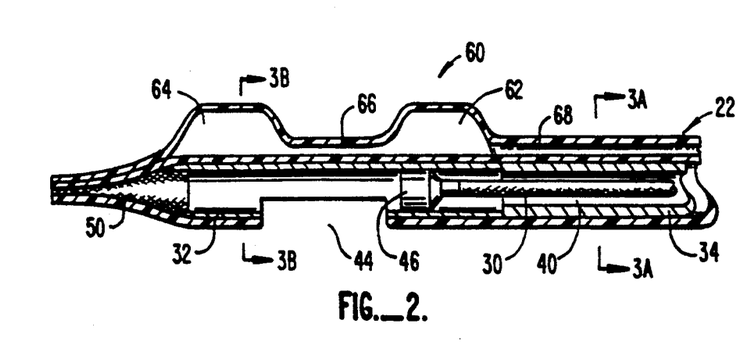
FIG. 2 is a side elevational view of the distal housing of the catheter illustrated in FIG. 1, shown in cross section.
Figure 3A:
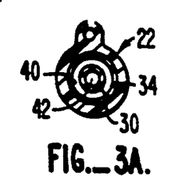
FIGS. 3A and 3B are cross-sectional views taken along lines 3A—3A and 3B—3B of FIG. 2, respectively.
Figure 3B:
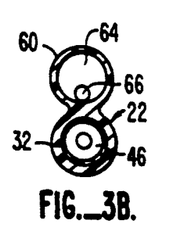

The cutter torque cable 30 extends through a lumen 40 defined within the catheter body 22, and has a diameter generally in the range from about 0.4 mm to 1.5 mm, usually being in the range from about 0.5 mm to 1.0 mm. Conveniently, the cutter torque cable 30 may be formed from multi-stranded stainless steel wire. If it is desired to pass a steerable guide wire through the center, the cutter torque cable 30 should be formed as a tube, typically a braided tube, such as a stainless steel braid coated with a plastic, such as a urethane. A central lumen 42 formed within the cutter torque cable 30 will then be available to receive the steerable guide wire.

The lumen 40 is connected with flush port 26 on manifold connector 16. During use of the atherectomy catheter 10, the flush port 26 will generally be connected to a suitable source of flushing solution.

Elongate housing 32 is generally a hollow, cylindrical structure which is fixedly attached to the distal end of flexible torque member 34, thus forming an extension thereof. The housing 32 will usually be a rigid structure, as described above, but may also be a flexible structure. The interactional means carried by the housing 32 includes an elongate aperture 44 which is formed on one side of the housing and a cup-shaped cutting blade 46 which is rotatably mounted within the interior thereof. The elongate aperture 44 will typically have a length in the range from about 5 mm to 45 mm and a width in the range from about 1 mm to 4 mm. The cutting blade 46 is attached to the distal end of the cutter torque cable 30 so that the blade may be rotated and axially translated by manipulation of the driver connection 28.

Although a cup-shaped cutting blade is illustrated, it will be appreciated that a variety of other rotatable interventional elements may be substituted. For example, the use of helical cutting blades as described in U.S. patent application Ser. No. 07/405,906, the disclosure of which has previously been incorporated herein by reference may be utilized. Other interventional elements, such as drills and the like, may also find use.

A flexible, open-ended tip 50 is attached to the distal end of housing 32, forming a continuous interior volume therewith. The interior volume of the tip 50 is capable of receiving and retaining stenotic material which is severed by blade 46 as it is brought forward within housing 32. Flexible tip 50 also facilitates positioning the catheter over a conventional guide wire which is received through lumen 42 in torque cable 30. The flexible tip 50 is conveniently formed from a braided material, typically braided stainless steel, and is attached to the cutter housing 32 by conventional means.

An inflatable bladder or balloon 60 is secured to housing 32 on a side generally opposite to that of aperture 44. The bladder 60 includes a first inflatable chamber 62 located at a proximal end of the housing 32 and a second inflatable chamber 64 located at a distal end of the housing. The chambers 62 and 64 are spaced apart but interconnected by a lumen 66 which spans the region therebetween. The first chamber 62 is connected to a lumen 68 formed in catheter body 22. The lumen 68, in turn, may be connected to a source of inflation medium (not illustrated) through the inflation port 24 on the proximal connector 16. In this way, the chambers 62 and 64 may be simultaneously inflated through the single lumen 68.

The inflatable bladder 60 may be conveniently formed as part of the catheter body 22 by the method described in copending application Ser. No. 07/449,014, the disclosure of which is incorporated herein by reference. Briefly, a tube including at least two axial lumens is extruded from a suitable thermoplastic material, such as a heat-shrinkable polyolefin, preferably being polyethylene or Surlyn ®. One of the lumens is expanded using hot air and internal pressure, and the flexible torque member 34 and housing 32 are inserted therein. Conveniently, a space maintainer (not illustrated), such as a teflon rod, may be inserted into the second lumen while the flexible torque member 34 and housing 32 are being inserted into the first lumen. The first lumen is then shrunk tightly about both the flexible torque member and the housing, as illustrated in FIGS. 1, 2, 3A and 3B. The distal portion of the second lumen may then be expanded using heated air under pressure to form the bladder or balloon 60. A central region of the bladder may then be shrunk or constricted in order to provide the connecting lumen 66 while retaining the expanded chambers 62 and 64. The portion of catheter body 22 which covers the aperture 44 after constriction will typically be cut away to fully expose the interior of housing 32. An adhesive can be applied around the window opening to further adhere the balloon firmly in place opposite the opening without applying adhesive to the inflatable portion of the balloon.

Figure 4:
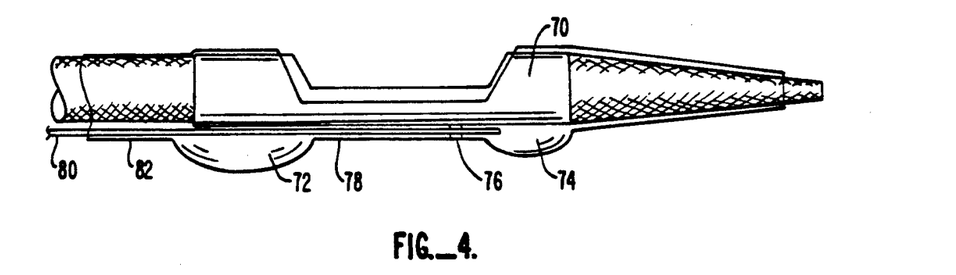
FIG. 4 is an elevational view of the distal end of an alternate embodiment of a catheter constructed in accordance with the principles of the present invention, where first and second inflatable chambers are expandable to different diameters.

Referring now to FIG. 4, a cutter housing 70 similar to that illustrated in FIGS. 1, 2, 3A and 3B may be provided with separately-inflatable balloon chambers 72 and 74 by isolating the chambers from one another and providing separate inflation lumens to each chamber. As illustrated, a plug 76 is provided within the connecting lumen 78, and a separate inflation lumen 80 extends through the primary inflation lumen 82, through the plug 76, and into the distal inflation chamber 74. This way, the proximal inflation chamber 72 may be inflated through the primary inflation lumen 82, while the distal inflation chamber 74 may be separately inflated through the second inflation lumen 80. As illustrated, the chambers 72 and 74 are sized differently, although such a design feature is unrelated to the chamber isolation.

Figure 5:
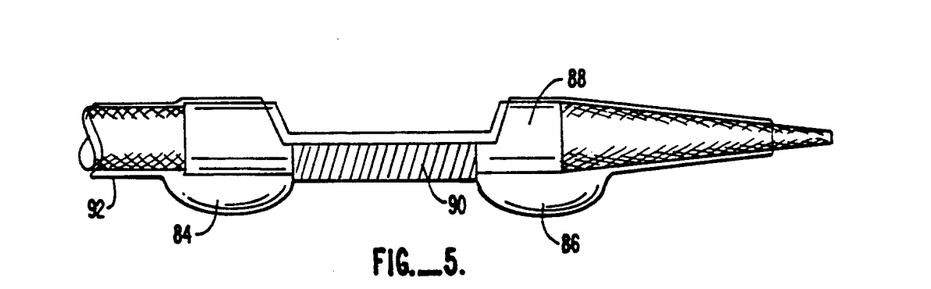
FIGS. 5 and 6 are elevational views of the distal end of a second alternate embodiment of a catheter constructed in accordance with the principles of the present invention, where first and second inflatable chambers are separated by an elastic constrictive member.
Figure 6:
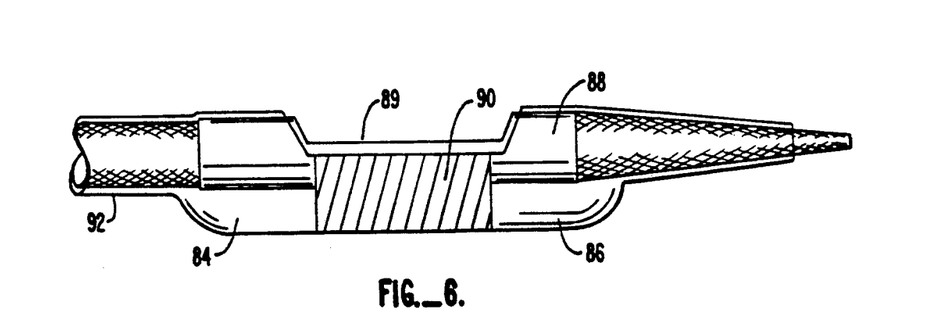

Referring now to FIGS. 5 and 6, inflatable chambers 84 and 86 may be formed from a single inflatable bladder extending from a proximal to a distal end of housing 88 by wrapping a constrictive band 90 around the middle of the bladder. The constrictive band 90 prevents inflation of the middle section of the bladder, allowing the regions formed forwardly and rearwardly of the band to inflate without restriction. A single inflation lumen 92 may be provided, in which case an inflation path between the chamber 84 and the chamber 86 must be left through the constricted region therebetween. Conveniently, a tube or other space maintainer (not illustrated) may be left between the chambers 84 and 86.

Preferably, the constrictive band 90 will be formed from an elastic material which allows the middle section of the bladder to inflate when the internal pressure exceeds a certain predetermined threshold. In this way, a single, continuous inflated volume, as illustrated in FIG. 6, may be provided when desired by increasing the inflation pressure to above said predetermined threshold level. Such a construction, in effort, provides a third inflatable chamber located between the two spaced-apart chambers which may be optionally inflated in order to change the position of the housing.

Figure 7:
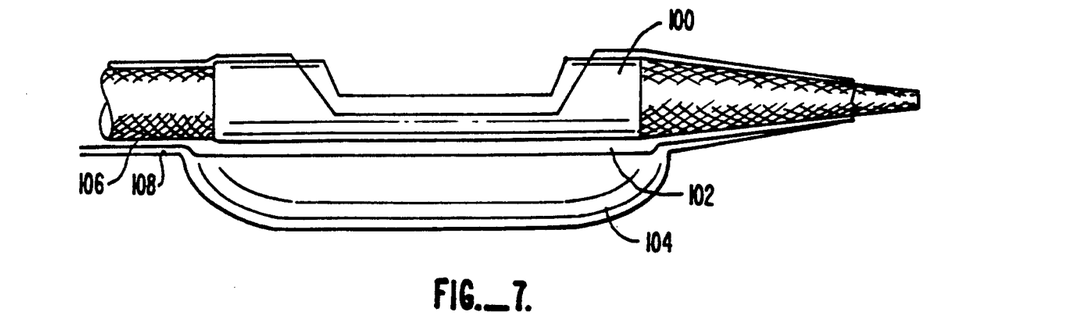
FIGS. 7 and 8 are elevational views of the distal end of a third alternate embodiment of a catheter constructed in accordance with the principles of the present invention, having first and second inflatable balloons present in a nested configuration.
Figure 8:
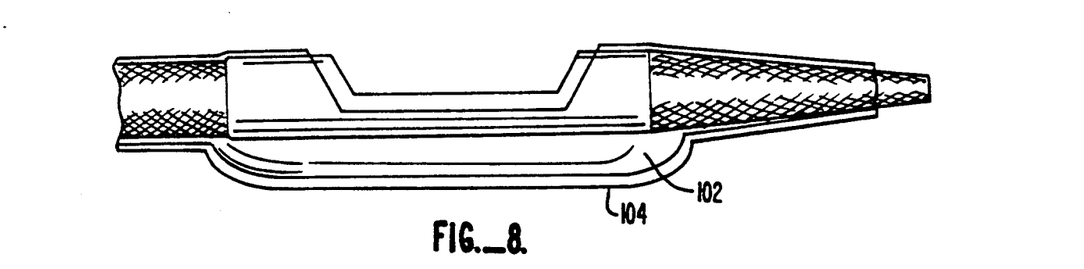

Referring now to FIGS. 7 and 8, a cutter housing 100 having a pair of nested balloons 102 and 104 is illustrated. The nested balloons 102 and 104 are separately inflatable through lumens 106 and 108, respectively. The outer balloon 104 is capable of being inflated to a larger size, as illustrated in FIG. 7, while the inner balloon 102 is capable of being inflated to a smaller size, as illustrated in FIG. 8. This way, the treating physician can select the degree to which the housing 100 is to be laterally deflected without risking overinflation or dilatation.

Figure 9:
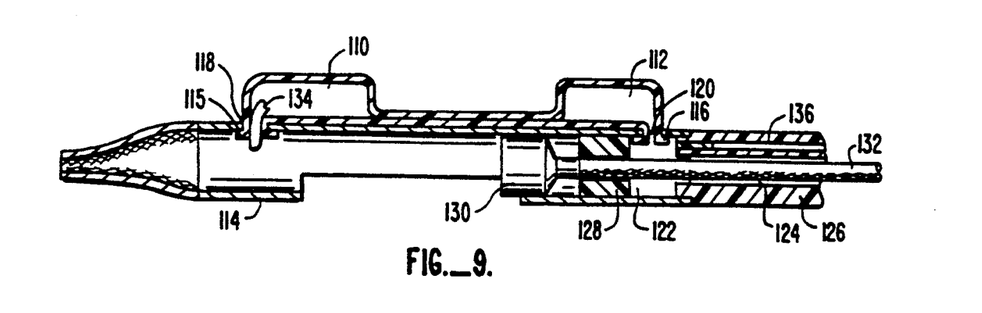
FIG. 9 is an elevational view of the distal end of a fourth alternate embodiment of a catheter constructed in accordance with the principles of the present invention, employing separate inflation lumens.
Figure 10:
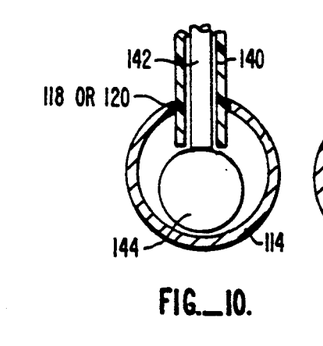
FIGS. 10–13 illustrate a particular method for attaching an inflatable balloon of the type illustrated in FIG. 9 to a catheter housing.

Referring now to FIG. 9, a particular embodiment having separately inflatable balloon chambers 110 and 112 secured to one side of a cutter housing 114 is illustrated. The inflatable chambers 110 and 112 are formed from a single extruded member wherein each inflatable chamber is expanded and the region between the inflatable chambers is sealed so that the chambers are isolated from each other. A flange element, 115 is formed at the end of the first chamber 110, while a similar flange member 116 is formed at the end of chamber 112. The flanges 115 and 116 are received through ports 118 and 120 formed through the side of the cutter housing 114, as explained in greater detail in connection with FIGS. 10–13.

A port in flange 116 opens into region 122 within the housing 114. Region 122, in turn, is open to central lumen 124 formed in the flexible catheter body 126. Region 122, however, is sealed from the remainder of housing 114 by a tubular seal 128 which is glued to the inner surface of housing 114. The cutter torque cable 132 is able to pass through the seal 128 so that a cutter 130 mounted on the distal end of the cable may be manipulated within the housing as described for previous embodiments. In this way, chamber 112 may be inflated through the central lumen 124 in the manner described in U.S. Pat. No. 4,669,469, the disclosure of which has been previously incorporated herein by reference. In particular, the forward inflatable chamber 112 is inflated through a tube 134 which passes in through flange 115. Tube 134, in turn, is connected to a separate inflation lumen 136 extending through catheter body 126.

Figure 11:
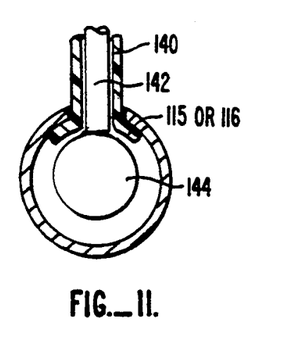
Figure 12:
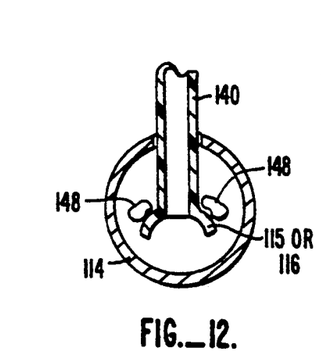
Figure 13:
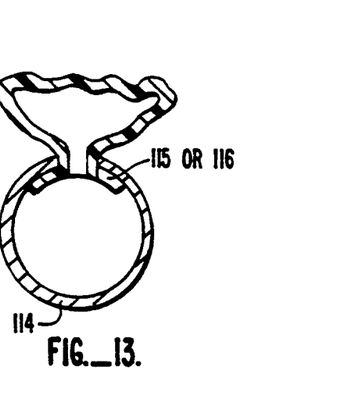

Referring now to FIGS. 10–13, the inflatable chambers 110 and 112 may be formed as follows. An extruded thermoplastic tube 140 is inserted through port 116 or 118 in housing 114, and a cold pin 142 is inserted through a central lumen thereof. A heated mandrel in the form of a cylindrical pin 144 is then inserted into the interior of housing 114 and pushed upward to contact the lower end of the pin 142 and form flange 115 or 116 in the end of tube 140, as illustrated in FIG. 11. The resulting flange 115 or 116 is generally in the shape of a saddle and conforms to the interior surface of the housing 114 in the region of port (inflation aperture) 116 or 118. Glue 148 is applied around the flange 115 and 116, as illustrated in FIG. 12, and the tube 140 is pulled upwards so that the flanges adhere to the interior of housing 114. After the glue sets and both ends of tube 140 are secured within ports 118 and 120, respectively, the tube may be expanded using hot air and molded into the desired profile, as illustrated in FIG. 9.

Figure 14:
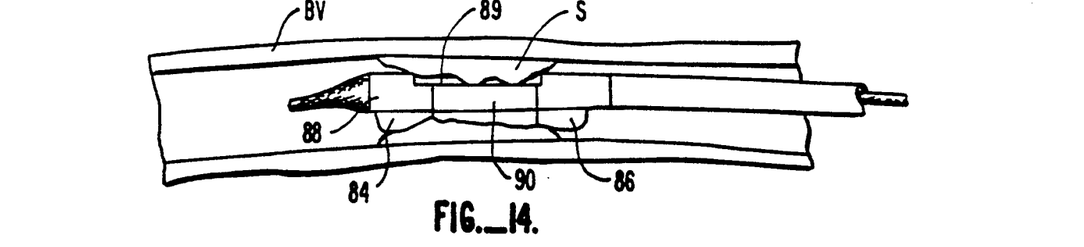
FIGS. 14 and 15 illustrate the use of a catheter constructed in accordance with the principles of the present invention for removing stenotic material from the stenosed region within a blood vessel.
Figure 15:
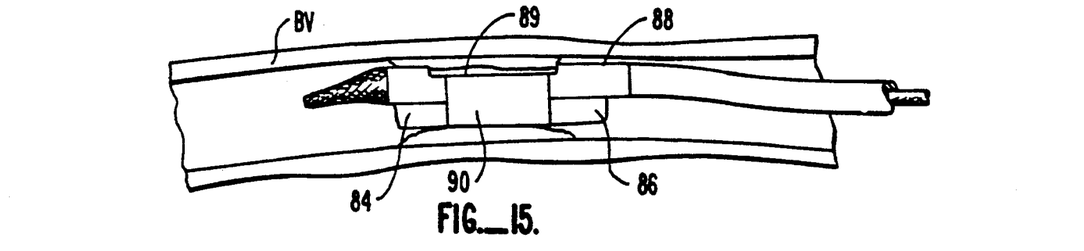

Referring now to FIGS. 14 and 15, use of the catheter of FIGS. 5 and 6 in removing stenotic material from a blood vessel BV is illustrated. The catheter housing 88 is positioned within the blood vessel BV so that the cutting aperture 89 lies proximate the region of stenosis S. Initially, inflatable chambers 84 and 86 are expanded using an inflation medium introduced through lumen 92 in a conventional manner. The two spaced-apart inflatable chambers 84 and 86 are stably positioned against the irregular surface of the blood vessel wall which lies opposite the stenosis S. The cutting blade (not illustrated) is then brought forward and a layer of the stenotic material excised and collected within the forward region of the catheter. Optionally, the housing 88 may be further urged in the direction of cutout 89 by expanding the constricting band 90 by increasing the inflation pressure. The expanded band 90 will press against the stenosis on the opposite wall of the blood vessel BV to cause additional stenotic material to enter the cutout, in turn allowing such additional material to be severed.

Figure 16:
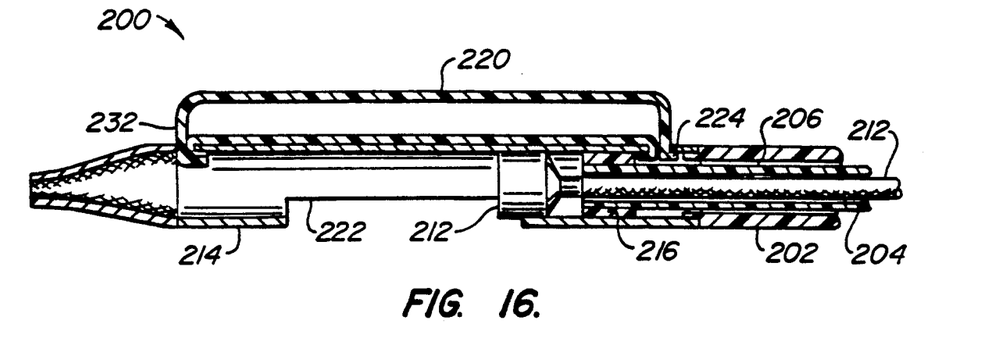
FIG. 16 is an elevational view of the distal end of a fifth alternate embodiment of a catheter constructed in accordance with the principles of the present invention, shown in cross-section.
Figure 17:
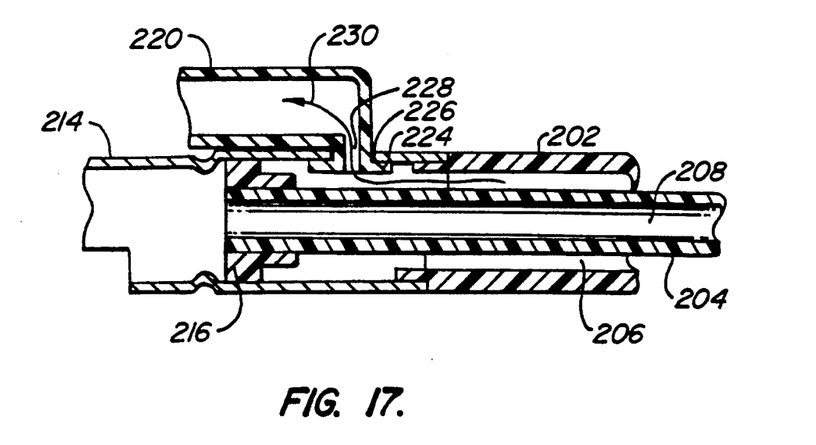
FIG. 17 is a detailed view of the integral flange connection joint of the inflatable balloon to the elongate housing of FIG. 16.

Referring now to FIGS. 16 and 17, a catheter 200 includes a catheter body 202 having an isolation tube 204 extending the entire length of a central lumen 206 thereof. A drive shaft 210 is rotatably and axially translatably mounted within a central lumen 208 of the isolation tube 204 and includes a cutting blade 212 at its distal end. The cutting blade 212 is disposed in cutter housing 214, and the interior of the housing 214 is isolated from the central lumen 206 by a spacer member 216 which serves additionally to hold the isolation tube 204 concentrically within the interior of lumen 206.

A balloon 220 is secured to the outside of housing 214, generally opposite to cutter aperture 222. The balloon 220 includes an integral flange structure 224 which is formed through an inflation aperture 226 present in the wall of housing 214, generally proximally of the spacer 216. In this way, inflation passage 228 defined by the flange structure 224 permits inflation medium to enter to balloon 220, generally as illustrated by arrow 230 in FIG. 17. The flange structure 224 can be formed by the method described in connection with FIGS. 10-13 hereinabove. A distal end 232 of balloon 220 can be secured to the distal end of housing 214 in a variety of ways. Conveniently, the end of the balloon 220 can be gathered and folded over into the interior of housing 214, as illustrated.

The balloon 220 can be formed into a desired geometry by internal heating and molding, in a conventional manner. The balloon 220 can be formed into two or more separate chambers, as illustrated in connection with FIG. 9, or can be formed into a single substantially continuous chamber, as illustrated in FIG. 16.

The catheter 200 of FIGS. 16 and 17 has certain advantages. First, the use of spacer 216 in combination with the isolation tube 204 permits the annular inflation lumen to be isolated from the interior of housing 214 without the need to utilize a sliding seal, such as seal 128 in FIG. 9. Thus, the advantage of a single lumen construction, such as that described in reissue patent Re. 33,569, can be substantially achieved without having to use the sliding seal which is subject to failure. Moreover, the integral flange structure 224 on balloon 220 provides a secure connection to the annular inflation lumen, where the connection is not likely to fail.

While the invention has been particularly shown and described with reference to preferred embodiments thereof, it will be understood by those skilled in the art that changes in form and detail may be made therein without departing from the spirit and scope of the invention.

What is claimed is:

1. A catheter comprising:
    a flexible catheter body having a proximal end, a distal end, and a lumen extending between the proximal and distal ends;
    an elongate housing having a proximal end and a distal end and being secured at its proximal end to the distal end of the catheter body;
    an interactional mechanism disposed on one side of the housing; and
    an inflatable balloon having a proximal end and a distal end and being secured to the housing on a side generally opposite to that of the interactional mechanism, wherein the balloon includes an integral flange structure which conforms to and is secured to an inner surface of the housing through an inflation aperture therein, whereby the balloon can be inflated through the lumen of the catheter body and the flange structure.

2. A catheter as in claim 1, wherein the housing includes an elongate aperture on the one side and the interactional mechanism includes a blade and a drive shaft for moving the blade past the aperture, said drive shaft being disposed in the lumen of the catheter body.

3. A catheter as in claim 2, further comprising an isolation tube having a proximal end and a distal end and extending between the distal and proximal ends of the flexible catheter body, wherein said isolation tube is disposed inside the lumen of the catheter body to receive the drive shaft and is secured at its distal end to the housing to define an annular inflation lumen which is isolated from the interior of the housing.

4. A catheter as in claim 1, wherein the inflatable balloon includes at least two spaced-apart inflation chambers.

5. A catheter as in claim 1, wherein the inflatable balloon consists of a single continuous chamber.

6. A catheter comprising:
    a flexible catheter body having a proximal end, a distal end, and a lumen extending between the proximal and distal ends;
    a substantially rigid elongate housing having a proximal end and a distal end and being secured at its proximal end to the distal end of the catheter body;
    an isolation tube having a proximal end, a distal end, and a lumen extending between said distal and proximal ends, wherein the isolation tube is disposed inside the lumen of the catheter body so that an outer surface of the isolation tube and inner surface of the catheter body lumen together, define an annular inflation lumen and wherein the isolation tube is secured at its distal end to the proximal end of the housing to isolate the housing from the annular inflation lumen; and
    an inflatable balloon having a proximal end and a distal end and being secured to the housing and connected to the annular inflation lumen, whereby the balloon can be inflated by applying an inflation medium to the proximal end of the annular lumen.

7. A catheter as in claim 6, wherein the inflatable balloon includes an integral flange structure which is secured to the elongate housing through an inflation aperture therein, said flange structure defining an inflation path between the annular lumen and the interior of the balloon.

8. A catheter as in claim 6, wherein the housing includes an elongate aperture on one side, a blade within the housing proximate the aperture, and a drive shaft for moving the blade past the aperture, said drive shaft being disposed in the lumen of the isolation tube.

9. A catheter as in claim 6, wherein the inflatable balloon includes at least two spaced-apart inflation chambers.

10. A catheter as in claim 6, wherein the inflatable balloon consists of a single continuous chamber.

11. A catheter comprising:
    a flexible catheter body having a proximal end, a distal end, and a lumen extending between the proximal and distal ends;

an elongate housing having a proximal end and a distal end and being secured at its proximal end to the distal end of the catheter body;

an interactional mechanism disposed on one side of the housing; and an inflatable balloon composed of a thermoplastic and having a proximal end and a distal end and being secured to the housing on a side generally opposite to that of the interactional mechanisms wherein the balloon includes an integral flange structure which is disposed through an inflation aperture in the housing and which has been formed against an interior surface of the housing by the contact with a heated mandrel, whereby the flange conforms to said interior surface and the balloon can be inflated through the lumen of the catheter body and the flange structure.

12. A catheter as in claim 11, wherein the housing includes an elongate aperture on the one side and the interaction mechanism includes a blade and a drive shaft for moving the blade past the aperture, said drive shaft being disposed in the lumen of the catheter body.

13. A catheter as in claim 12, further comprising an isolation tube having a proximal end and a distal end extending between the distal and proximal ends of the flexible catheter body, wherein said isolation tube is disposed inside the lumen of the catheter body to receive the drive shaft and is secured at its distal end to the housing to define an annular inflation lumen which is isolated form the interior of the housing.

14. A catheter as in claim 11, wherein the inflatable balloon includes at least two spaced-apart inflation chambers.

15. A catheter as in claim 11, wherein the inflatable balloon consists of a single continuous chamber.

* * * * *